United States Patent
Al-Ali et al.

(10) Patent No.: US 9,161,713 B2
(45) Date of Patent: Oct. 20, 2015

(54) MULTI-MODE PATIENT MONITOR CONFIGURED TO SELF-CONFIGURE FOR A SELECTED OR DETERMINED MODE OF OPERATION

(71) Applicant: Masimo Corporation, Irvine, CA (US)

(72) Inventors: Ammar Al-Ali, San Juan Capistrano, CA (US); Massi Joe E. Kiani, Laguna Niguel, CA (US); Walter M. Weber, Laguna Hils, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 13/721,497

(22) Filed: Dec. 20, 2012

(65) Prior Publication Data

US 2013/0109935 A1 May 2, 2013

Related U.S. Application Data (63) Continuation of application No. 12/254,748, filed on Oct. 20, 2008, now Pat. No. 8,337,403, which is a continuation of application No. 11/071,875, filed on Mar. 3, 2005, now Pat. No. 7,438,683.

(60) Provisional application No. 60/549,996, filed on Mar. 4, 2004.

(51) Int. Cl.
*A61B 5/00* (2006.01)
*G06F 3/00* (2006.01)
(Continued)

(52) U.S. Cl.
CPC ............ *A61B 5/14551* (2013.01); *G06F 3/002* (2013.01); *G06F 19/3406* (2013.01);
(Continued)

(58) Field of Classification Search
CPC .......... A61B 5/14551; A61B 2560/02; A61B 2560/0406; A61B 2560/04; A61B 2560/0487; A61B 2505/01; A61B 2505/03; A61B 2505/05; G06F 3/002; G06F 19/3406; G06F 19/3412
See application file for complete search history.

(56) References Cited

U.S. PATENT DOCUMENTS

| | | |
|---|---|---|
| 4,051,522 A | 9/1977 | Healy |
| 4,085,378 A | 4/1978 | Ryan |

(Continued)

FOREIGN PATENT DOCUMENTS

| | | |
|---|---|---|
| DE | 3328862 A1 | 2/1985 |
| EP | 0104771 B1 | 4/1984 |

(Continued)

OTHER PUBLICATIONS

Malviya, S. et al in "False Alarms and Sensitifity of Conventional Pulse Oximetry Versus the Masimo SET™ Technology in the Pediatric Postanesthesia Care Unit", Anesth Analg 2000;90, p. 1336-1340.

(Continued)

*Primary Examiner* — Gary Jackson
*Assistant Examiner* — Marie Archer
(74) *Attorney, Agent, or Firm* — Knobbe, Martens, Olson & Bear LLP (57) ABSTRACT

A patient monitoring system comprises a plurality of emitters configured to transmit light into a tissue site and a detector configured to receive the light after tissue absorption. The detector generates a signal responsive to the intensity of the light and communicates the signal to a monitor. An information element is readable by the monitor so as to identify an environment of use. An actuator may preset at least one user-selectable operational parameter of the monitor in response to the information element.

16 Claims, 1 Drawing Sheet

(51) Int. Cl.
  *G06F 19/00* (2011.01)
  *A61B 5/1455* (2006.01)
(52) U.S. Cl.
  CPC ......... *G06F19/3412* (2013.01); *A61B 2505/01* (2013.01); *A61B 2560/02* (2013.01); *A61B 2560/0487* (2013.01); *A61B 2562/08* (2013.01)

(56) References Cited

U.S. PATENT DOCUMENTS

| | | | |
|---|---|---|---|
| 4,623,248 A | 11/1986 | Sperinde |
| 4,653,498 A | 3/1987 | New |
| 4,745,398 A | 5/1988 | Abel |
| 4,765,340 A | 8/1988 | Sakai |
| 4,800,495 A | 1/1989 | Smith |
| 4,802,486 A | 2/1989 | Goodman |
| 4,863,265 A | 9/1989 | Flower |
| 4,870,588 A | 9/1989 | Merhav |
| 4,911,167 A | 3/1990 | Corenman |
| 4,934,372 A | 6/1990 | Corenman et al. |
| 4,942,877 A | 7/1990 | Sakai |
| 4,955,379 A | 9/1990 | Hall |
| 4,960,128 A | 10/1990 | Gordon et al. |
| 4,964,408 A | 10/1990 | Hink et al. |
| 4,965,840 A | 10/1990 | Subbarao |
| 5,003,252 A | 3/1991 | Nystrom |
| RE33,643 E | 7/1991 | Isaacson |
| 5,041,187 A | 8/1991 | Hink et al. |
| 5,069,213 A | 12/1991 | Polczynski |
| 5,069,214 A | 12/1991 | Samaras et al. |
| 5,163,438 A | 11/1992 | Gordon et al. |
| 5,170,791 A | 12/1992 | Boos et al. |
| 5,188,108 A | 2/1993 | Secker |
| 5,190,038 A | 3/1993 | Polson |
| 5,193,124 A | 3/1993 | Subbarao |
| 5,206,807 A | 4/1993 | Hatke et al. |
| 5,218,962 A | 6/1993 | Mannheimer |
| 5,226,417 A | 7/1993 | Swedlow |
| 5,246,002 A | 9/1993 | Prosser |
| 5,259,381 A | 11/1993 | Cheung |
| 5,262,944 A | 11/1993 | Weisner et al. |
| 5,270,942 A | 12/1993 | Reed |
| 5,307,284 A | 4/1994 | Brunfeldt |
| 5,319,355 A | 6/1994 | Russek |
| 5,331,394 A | 7/1994 | Shalon et al. |
| 5,337,744 A | 8/1994 | Branigan |
| 5,341,805 A | 8/1994 | Stavridi et al. |
| 5,345,510 A | 9/1994 | Singhi |
| 5,348,004 A | 9/1994 | Hollub |
| 5,353,356 A | 10/1994 | Waugh et al. |
| 5,355,882 A | 10/1994 | Ukawa |
| 5,357,965 A | 10/1994 | Hall et al. |
| 5,368,224 A | 11/1994 | Richardson |
| D353,195 S | 12/1994 | Savage et al. |
| D353,196 S | 12/1994 | Savage et al. |
| 5,377,676 A | 1/1995 | Vari et al. |
| 5,384,451 A | 1/1995 | Smith et al. |
| 5,398,003 A | 3/1995 | Heyl et al. |
| 5,404,003 A | 4/1995 | Smith |
| 5,406,952 A | 4/1995 | Barnes |
| D359,546 S | 6/1995 | Savage et al. |
| 5,421,329 A | 6/1995 | Casciani |
| 5,431,170 A | 7/1995 | Mathews |
| D361,840 S | 8/1995 | Savage et al. |
| 5,438,983 A | 8/1995 | Falcone |
| 5,442,940 A | 8/1995 | Secker |
| D362,063 S | 9/1995 | Savage et al. |
| 5,448,991 A | 9/1995 | Polson |
| 5,452,717 A | 9/1995 | Branigan et al. |
| D363,120 S | 10/1995 | Savage et al. |
| 5,456,252 A | 10/1995 | Vari et al. |
| 5,473,536 A | 12/1995 | Wimmer |
| 5,479,934 A | 1/1996 | Imran |
| 5,481,620 A | 1/1996 | Vaidyanathan |
| 5,482,036 A | 1/1996 | Diab et al. |
| 5,490,505 A | 2/1996 | Diab et al. |
| 5,494,043 A | 2/1996 | O'Sullivan et al. |
| 5,503,148 A | 4/1996 | Pologe |
| 5,533,511 A | 7/1996 | Kaspari et al. |
| 5,534,851 A | 7/1996 | Russek |
| 5,542,421 A | 8/1996 | Erdman |
| 5,549,111 A | 8/1996 | Wright et al. |
| 5,561,275 A | 10/1996 | Savage et al. |
| 5,562,002 A | 10/1996 | Lalin |
| 5,575,284 A | 11/1996 | Athan |
| 5,588,435 A | 12/1996 | Weng et al. |
| 5,590,649 A | 1/1997 | Caro et al. |
| 5,602,924 A | 2/1997 | Durand et al. |
| 5,608,820 A | 3/1997 | Vaidyanathan |
| 5,610,996 A | 3/1997 | Eller |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,652,566 A | 7/1997 | Lambert |
| 5,685,299 A | 11/1997 | Diab et al. |
| 5,720,293 A | 2/1998 | Quinn |
| D393,830 S | 4/1998 | Tobler et al. |
| 5,743,262 A | 4/1998 | Lepper |
| 5,750,329 A | 5/1998 | Quinn et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,237 A | 7/1998 | Casciani |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,820,267 A | 10/1998 | Bryars |
| 5,823,950 A | 10/1998 | Diab et al. |
| 5,830,131 A | 11/1998 | Caro et al. |
| 5,833,618 A | 11/1998 | Caro et al. |
| 5,842,979 A | 12/1998 | Jarman |
| 5,853,364 A | 12/1998 | Baker, Jr. et al. |
| 5,860,918 A | 1/1999 | Schradi et al. |
| 5,860,919 A | 1/1999 | Kiani-Azarbayjany et al. |
| 5,865,736 A | 2/1999 | Baker, Jr. et al. |
| 5,890,929 A | 4/1999 | Mills et al. |
| 5,891,023 A | 4/1999 | Lynn |
| 5,904,654 A | 5/1999 | Wohltmann et al. |
| 5,919,134 A | 7/1999 | Diab |
| 5,921,921 A | 7/1999 | Potratz et al. |
| 5,934,925 A | 8/1999 | Tobler et al. |
| 5,940,182 A | 8/1999 | Lepper, Jr. et al. |
| 5,950,139 A | 9/1999 | Korycan |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,047,203 A | 4/2000 | Sackner et al. |
| 6,064,910 A | 5/2000 | Andersson et al. |
| 6,067,462 A | 5/2000 | Diab et al. |
| 6,081,735 A | 6/2000 | Diab et al. |
| 6,083,156 A | 7/2000 | Lisiecki |
| 6,083,172 A | 7/2000 | Baker, Jr. et al. |
| 6,088,607 A | 7/2000 | Diab et al. |
| 6,110,522 A | 8/2000 | Lepper, Jr. et al. |
| 6,119,026 A | 9/2000 | McNulty et al. |
| 6,122,535 A | 9/2000 | Kaestle et al. |
| 6,124,597 A | 9/2000 | Shehada |
| 6,128,521 A | 10/2000 | Marro et al. |
| 6,129,675 A | 10/2000 | Jay |
| 6,135,952 A | 10/2000 | Coetzee |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,188,407 B1 | 2/2001 | Smith et al. |

(56) References Cited

U.S. PATENT DOCUMENTS

| | | | |
|---|---|---|---|
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,421,549 B1 | 7/2002 | Jacques |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Al Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,628,975 B1 | 9/2003 | Fein et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,708,049 B1 * | 3/2004 | Berson et al. ............... 600/323 |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,801,798 B2 | 10/2004 | Geddes et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,311,666 B2 | 12/2007 | Stupp et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,440,787 B2 | 10/2008 | Diab |

(56) References Cited

U.S. PATENT DOCUMENTS

| | | |
|---|---|---|
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,255,026 B1 | 8/2012 | Al-Ali |
| 8,255,028 B2 | 8/2012 | Al-Ali et al. |
| 8,260,577 B2 | 9/2012 | Weber et al. |
| 8,274,360 B2 | 9/2012 | Sampath et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 7,438,683 B2 | 11/2013 | Al-Ali et al. |
| 8,577,431 B2 | 11/2013 | Lamego et al. |
| 8,581,732 B2 | 11/2013 | Al-Ali et al. |

(56) References Cited

U.S. PATENT DOCUMENTS

| | | |
|---|---|---|
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 2002/0082488 A1 | 6/2002 | Al-Ali |
| 2002/0161291 A1 | 10/2002 | Kianl |
| 2003/0000522 A1 | 1/2003 | Lynn |
| 2003/0018241 A1 | 1/2003 | Mannheimer |
| 2003/0073890 A1 | 4/2003 | Hanna |
| 2003/0120164 A1 | 6/2003 | Nielsen |
| 2004/0152954 A1* | 8/2004 | Pearce et al. .................. 600/300 |
| 2004/0204635 A1 | 10/2004 | Scharf et al. |
| 2009/0247924 A1 | 10/2009 | Lamego et al. |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0261979 A1 | 10/2010 | Kiani |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |

(56) References Cited

U.S. PATENT DOCUMENTS

| | | |
|---|---|---|
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

FOREIGN PATENT DOCUMENTS

| | | |
|---|---|---|
| EP | 0352923 | 1/1990 |
| EP | 0645117 | 3/1995 |
| EP | 0659384 | 6/1995 |
| WO | WO 84/03032 | 8/1984 |
| WO | WO 92/11803 | 7/1992 |
| WO | WO 92/15955 | 9/1992 |
| WO | WO 92/20273 | 11/1992 |
| WO | WO 95/21567 | 8/1995 |
| WO | WO 98/43071 | 10/1998 |

OTHER PUBLICATIONS

Rheineck, A.T. et al. In "Advanced Pulse Oximeter Signal Processing Technology Compared to Simple Averaging. II. Effect on Frequency of Alarms in the Postanesthesia Care Unit", Journal of Clinical Anesthesia 11, p. 196-200, 1999.

Rheineck, A.T. et al. in "Advanced Pulse Oximeter Signal Processing Technology Compared to Simple Averaging. I. Effect on Frequency of Alarms in the Operating Room", Journal of Clinical Anesthesia 11:192-195, 1999.

NPL_Pulse_Oximetry_study.pdf, pp. 1-28.

Lie, C. et al., in "Comparison of the Nellcor 200 and N-300 pulse oximeters during simulated postoperative activities", Anesthesia, May 1997, 52(5):450-452 (Abstract), p. 1.

8,845,543, Sep. 2014, Diab et al.

U.S. Appl. No. 90/012,403, filed Jul. 23, 2012, requesting *ex parte* reexamination of U.S. Pat. No. 6,263,222, including accompanying Reexam Request, claim charts, and other documentation filed under 37 C.F.R. § 1.510 and 35 U.S.C. § 302.

U.S. Appl. No. 90/012,409, filed Aug. 17, 2012, requesting *ex parte* reexamination of U.S. Pat. No. 6,699,194, including accompanying Reexam Request, claim charts, and other documentation filed under 37 C.F.R. § 1.510 and 35 U.S.C. § 302.

U.S. Appl. No. 90/012,463, filed Sep. 5, 2012, requesting *ex parte* reexamination of U.S. Pat. No. 7,215,984, including accompanying Reexam Request, claim charts, and other documentation filed under 37 C.F.R. § 1.510 and 35 U.S.C. § 302.

U.S. Appl. No. 90/012,532, filed Sep. 13, 2012, requesting *ex parte* reexamination of U.S. Pat. No. 7,499,835, including accompanying Reexam Request, claim charts, and other documentation filed under 37 C.F.R. § 1.510 and 35 U.S.C. § 302.

U.S. Appl. No. 90/012,534, filed Sep. 13, 2012, requesting *ex parte* reexamination of U.S. Pat. No. 7,962,188, including accompanying Reexam Request, claim charts, and other documentation filed under 37 C.F.R. § 1.510 and 35 U.S.C. § 302.

U.S. Appl. No. 90/012,538, filed Sep. 13, 2012, requesting *ex parte* reexamination of U.S. Pat. No. 7,377,899, including accompanying Reexam Request, claim charts, and other documentation filed under 37 C.F.R. § 1.510 and 35 U.S.C. § 302.

U.S. Appl. No. 90/012,541, filed Sep. 13, 2012, requesting *ex parte* reexamination of U.S. Pat. No. 7,899,507, including accompanying Reexam Request, claim charts, and other documentation filed under 37 C.F.R. § 1.510 and 35 U.S.C. § 302.

U.S. Appl. No. 90/012,542, filed Sep. 13, 2012, requesting *ex parte* reexamination of U.S. Pat. No. 8,180,420, including accompanying Reexam Request, claim charts, and other documentation filed under 37 C.F.R. § 1.510 and 35 U.S.C. § 302.

U.S. Appl. No. 90/012,543, filed Sep. 13, 2012, requesting *ex parte* reexamination of U.S. Pat. No. 6,850,787, including accompanying Reexam Request, claim charts, and other documentation filed under 37 C.F.R. § 1.510 and 35 U.S.C. § 302.

U.S. Appl. No. 90/012,548, filed Sep. 13, 2012, requesting *ex parte* reexamination of U.S. Pat. No. 7,880,606, including accompanying Reexam Request, claim charts, and other documentation filed under 37 C.F.R. § 1.510 and 35 U.S.C. § 302.

U.S. Appl. No. 90/012,551, filed Sep. 13, 2012, requesting *ex parte* reexamination of U.S. Pat. No. 6,970,792, including accompanying Reexam Request, claim charts, and other documentation filed under 37 C.F.R. § 1.510 and 35 U.S.C. § 302.

U.S. Appl. No. 90/012,553, filed Sep. 13, 2012, requesting *ex parte* reexamination of U.S. Pat. No. 7,024,233, including accompanying Reexam Request, claim charts, and other documentation filed under 37 C.F.R. § 1.510 and 35 U.S.C. § 302.

U.S. Appl. No. 90/012,555, filed Sep. 13, 2012, requesting *ex parte* reexamination of U.S. Pat. No. 7,440,787, including accompanying Reexam Request, claim charts, and other documentation filed under 37 C.F.R. § 1.510 and 35 U.S.C. § 302.

U.S. Appl. No. 90/012,557, filed Sep. 13, 2012, requesting *ex parte* reexamination of U.S. Pat. No. 8,150,487, including accompanying Reexam Request, claim charts, and other documentation filed under 37 C.F.R. § 1.510 and 35 U.S.C. § 302.

U.S. Appl. No. 90/012,559, filed Sep. 13, 2012, requesting *ex parte* reexamination of U.S. Pat. No. 8,190,223, including accompanying Reexam Request, claim charts, and other documentation filed under 37 C.F.R. § 1.510 and 35 U.S.C. § 302.

U.S. Appl. No. 90/012,561, filed Sep. 14, 2012, requesting *ex parte* reexamination of U.S. Pat. No. 8,019,400, including accompanying Reexam Request, claim charts, and other documentation filed under 37 C.F.R. § 1.510 and 35 U.S.C. § 302.

U.S. Appl. No. 90/012,562, filed Sep. 14, 2012 requesting *ex parte* reexamination of U.S. Pat. No. 6,463,311, including accompanying Reexam Request, claim charts, and other documentation filed under 37 C.F.R. § 1.510 and 35 U.S.C. § 302.

U.S. Appl. No. 90/012,566, filed Sep. 14, 2012, requesting *ex parte* reexamination of U.S. Pat. No. 7,530,955, including accompanying Reexam Request, claim charts, and other documentation filed under 37 C.F.R. § 1.510 and 35 U.S.C. § 302.

U.S. Appl. No. 90/012,567, filed Sep. 14, 2012, requesting *ex parte* reexamination of U.S. Pat. No. 6,684,090, including accompanying Reexam Request, claim charts, and other documentation filed under 37 C.F.R. § 1.510 and 35 U.S.C. § 302.

U.S. Appl. No. 90/012,568, filed Sep. 14, 2012, requesting *ex parte* reexamination of U.S. Pat. No. 8,128,572, including accompanying (56) References Cited

OTHER PUBLICATIONS

Reexam Request, claim charts, and other documentation filed under 37 C.F.R. § 1.510 and 35 U.S.C. § 302.
U.S. Appl. No. 90/012,699, filed Oct. 4, 2012, requesting *ex parte* reexamination of U.S. Pat. No. 6,002,952, including accompanying Reexam Request, claim charts, and other documentation filed under 37 C.F.R. § 1.510 and 35 U.S.C. § 302.
U.S. Appl. No. 95/002,183, filed Sep. 12, 2012, requesting *inter partes* reexamination of U.S. Pat. No. 7,530,955, including accompanying Reexam Request, claim charts, and other documentation filed under 37 C.F.R. § 1.913 and 35 U.S.C. § 311.
Maciej Niedzwiecki et al. "Smoothing of Discontinuous Signals: The Competitive Approach," *IEEE Transactions on Signal Processing*, vol. 43, No. 1, Jan. 1995, pp. 1-13.
Declaration of Perry D. Oldham in Support of Masimo Opposition to Defendant's Motion for Summary Judgment of Invalidity and Noninfringement of U.S. Pat. No. 7,215,984, vol. 1, Doc. 556, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Perry D. Oldham in Support of Masimo's Opposition to Defendant's Motion for Summary Judgment of Invalidity and Noninfringement of U.S. Pat. No. 7,215,984, vol. 2, Doc. 558, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Masimo Corporation's Answering Brief in Opposition to Defendant's Motion for Summary Judgment of Invalidity and Noninfringement of U.S. Pat. No. 7,215,984, Doc. 555, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Philip's Opening Brief in Support of Defendant's Motion for Summary Judgment of Invalidity and Nonigringement of U.S. Pat. No. 7,215,984, Doc. 442, *Masimo Corporation v. Philips Electronics North America Corporation and Philips Medizin Systeme Böblingen GMBH*, (District of Delaware, Case No. 1:09-cv-00080 (LPS/MPT) dated Aug. 21, 2012. (Redacted).
Philip Defendant's Motion for Summary Judgment of Invalidity and Noninfringement of U.S. Pat. No. 7,215,984, Doc. 394, *Masimo Corporation v. Philips Electronics North America Corporation and Philips Medizin Systeme BOblingen GMBH*, (District of Delaware, Case No. 1:09-cv-00080 (LPS/MPT) dated Aug. 14, 2012.
Reply Brief in Support of Defendants' Motion for Summary Judgment of invalidity and Noninfringement of U.S. Pat. No. 7,216,984, Doc. 609, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012. (Redacted).
Declaration of Gail Baura, Ph.D. In Support of Masimo's Opposition to Defendant's Motion for Summary Judgment of Invalidity of U.S. Pat. No. 7,215,984, Doc. 561, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Gail Baura, Ph.D. in Support of Masimo's Opposition to Defendant's Motion for Summary Judgment of Invalidity of U.S. Patent No. 5,632,272, Doc. 554, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Perry D. Oldham in Support of Masimo Opposition to Defendant's Motion for Summary Judgment of Invalidity of U.S. Pat. No. 5,632,272, Doc. 553, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Masimo Corporation's Answering Brief in Opposition to Defendant's Motion for Summary Judgment of Invalidity and Noninfringement of U.S. Pat. No. 5,632,272, Doc. 552, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Opening Brief in Support of Defendants' Motion for Summary Judgment of Invalidity and Noninfringement of U.S. Pat. No. 5,632,272, Doc. 444, *Masimo Corporation v. Philips Electronics North America Corporation and Philips Medizin Systeme Böblingen GMBH*, (District of Delaware, Case No. 1:09-cv-00080 (LPS/MPT) dated Aug. 21, 2012. (Redacted).
Defendants' Motion for Summary Judgment of Invalidity and Noninfringement of U.S. Pat. No. 5,632,272, Doc. 402, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Reply Brief in Support of Defendants' Motion for Summary Judgment of Invalidity and Noninfringement of U.S. Pat. No. 5,632,272, Doc. 614, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012 (Redacted).
Declaration of Mohammed K. Diab in Support of Masimo's Oppositions to Defendants' Motions for Summary Judgment of Invalidity and Noninfringement of U.S. Pat. Nos. 5,632,272 and 7,215,984, Doc. 563, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012 (Redacted).
Declaration of Perry D. Oldham in Support of Masimo's Opposition to Defendant's Motion for Summary Judgment of Invalidity of U.S. Pat. No. 6,263,222, Doc. 550, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012 (Redacted).
Masimo Corporation's Answering Brief in Opposition to Defendants' Motion for Summary Judgment of Invalidity of U.S. Pat. No. 6,263,222, Doc. 549, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012 (Redacted).
Philips' Opening Brief in Support of Defendants' Motion for Summary Judgment of Invalidity of U.S. Pat. No. 6,263,222, Doc. 413, *Masimo Corporation v. Philips Electronics North America Corporation and Philips Medizin Systeme Böblingen GMBH*, (District of Delaware, Case No. 1:09-cv00080 (LPS/MPT) dated Aug. 14, 2012.
Defendants' Motion for Summary Judgment of Invalidity of U.S. Patent No. 6,263,222, Doc. 410, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Reply Brief in Support of Defendants' Motion for Summary Judgment of Invalidity of U.S. Pat. No. 6,263,222, Doc. 613, *Masimo Corporation v. Philips Electronics North America Corporation and Philips Medizin Systeme Boblingen GMBH*, (District of Delaware, Case No. 1:09-cv-00080 (LPS/MPT) dated Oct. 26, 2012 (Redacted).
Declaration of Gail Baura, Ph.D. in Support of Masimo's Opposition to Defendant's Motion for Summary Judgment of Invalidity of U.S. Pat. No. 6,263,222, Doc. 551, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Gail Baura, Ph.D. in Support of Masimo's Opposition to Defendant's Motion for Summary Judgment of Invalidity of U.S. Pat. No. 6,699,194, Doc. 508, *Masimo Corporation v. Philips Electronics North America Corporation and Philips Medizin Systeme Boblingen GMBH*, (District of Delaware, Case No. 1:09-cv-00080 (LPS/MPT) dated Sep. 21, 2012.
Opening Brief in Support of Defendants' Motion for Summary Judgment of Invalidity of U.S. Pat. No. 6,699,194, Doc. Doc 445, *Masimo Corporation v. Philips Electronics North America Corporation and*

(56) References Cited

OTHER PUBLICATIONS

*Philips Medizin Systeme Böblingen GMBH*, (District of Delaware, Case No. 1:09-cv-00080 (LPS/MPT) dated Aug. 21, 2012. (Redacted).
Defendants' Motion for Summary Judgment of Invalidity of U.S. Pat. No. 6,699,194, Doc. 406, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Reply Brief in Support of Defendants' Motion for Summary Judgment of Invalidity of U.S. Patent No. 6,699,194, Doc. 610, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012. (Redacted).
Declaration of Perry D. Oldham in Support of Masimo Opposition to Defendant's Motion for Summary Judgment of Invalidity of U.S. Pat. No. 6,699,194, Doc. 548, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Philips' Response to Masimo Corporation's Objections to the Report and Recommendation Regarding Claim Construction, Doc. 230, *Masimo Corporation v. Philips Electronics North America Corporation and Philips Medizin Systeme Böblingen GMBH*, (District of Delaware, Case No. 1:09-cv-00080 (LPS/MPT) dated Mar. 24, 2011.
Masimo Corporation's Objections to the Report and Recommendation Regarding Claim Construction, Doc. 219, *Masimo Corporation v. Philips Electronics North America Corporation and Philips Medizin Systeme Böblingen GMBH*, (District of Delaware, Case No. 1:09-cv-00080 (LPS/MPT) dated Mar. 8, 2011.
Defendants' Objections to Magistrate Judge Thynge's Report and Recommendation Regarding Claim.Construction, Doc. 218, *Masimo Corporation v. Philips Electronics North America Corporation and Philips Medizin Systeme Böblingen GMBH*, (District of Delaware, Case No. 1:09-cv-00080 (LPS/MPT) dated Mar. 7, 2011.
Report and Recommendation Regarding Claim Construction, Doc. 210, *Masimo Corporation v. Philips Electronics North America Corporation and Philips Medizin Systeme Böblingen GMBH*, (District of Delaware, Case No. 1:09-cv-00080 (LPS/MPT) dated Feb. 18, 2011.
Memorandum Order Adopting Report and Recommendation Regarding Claim Construction, Doc. 319, *Masimo Corporation v. Philips Electronics North America Corporation and Philips Medizin Systeme Böblingen GMBH*, (District of Delaware, Case No. 1:09-cv-00080 (LPS/MPT) dated Jan. 17, 2011.
Masimo Corporation's Response to Defendants' Objections to the Report and Recommendation Regarding Claim Construction, Doc. 232, *Masimo Corporation v. Philips Electronics North America Corporation and Philips Medizin Systeme Böblingen GMBH*, (District of Delaware, Case No. 1:09-cv-00080 (LPS/MPT) dated Mar. 24, 2011.
Supplemental Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated Mar. 18, 2012.
Appendixes for Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated Mar. 7, 2012.
Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated Mar. 7, 2012.
Revised Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Phillips Medizin Systeme Böblingen GMBH*, (District of Delaware, Case No. 1:09-cv-00080 (LPS/MPT) dated Mar. 7, 2012.
Second Amended Complaint for Patent Infringement, Doc. 42, *Masimo Corporation v. Philips Electronics North America Corporation and Philips Medizin Systeme Böblingen GMBH*, (District of Delaware, Case No. 1:11-cv-00742 (LPS/MPT) dated Apr. 25, 2012.
Masimo's Answer to Philips' Counterclaims, Doc. 28, *Masimo Corporation v. Philips Electronics North America Corporation and Philips Medizin Systeme Böblingen GMBH*, (District of Delaware, Case No. 1:11-cv-00742 (LPS/MPT) dated Dec. 30, 2011.
Defendants' Answer and Philips Electronics North America Corp.'s Counterclaims to Masimo's First Amended Complaint, Doc. 11, *Masimo Corporation v. Philips Electronics North America Corporation and Philips Medizin Systeme Böblingen GMBH*, (District of Delaware, Case No. 1:11-cv-00742 (LPS/MPT) dated Nov. 7, 2011.
Masimo's Answer to Philips' Counterclaims to Masimo's Second Amended Complaint, Doc. 358, *Masimo Corporation v. Philips Electronics North America Corporation and Philips Medizin Systeme Böblingen GMBH*, (District of Delaware, Case No. 1:11-cv-00742 (LPS/MPT) dated Jun. 4, 2012.
Defendants' Answer and Philips Electronics North America Corp.'s Counterclaims to Masimo's Second Amended Complaint, Doc. 43, *Masimo Corporation v. Philips Electronics North America Corporation and Philips Medizin Systeme Böblingen GMBH*, (District of Delaware, Case No. 1:11-cv-00742 (LPS/MPT) dated May 11, 2012.

\* cited by examiner

MULTI-MODE PATIENT MONITOR CONFIGURED TO SELF-CONFIGURE FOR A SELECTED OR DETERMINED MODE OF OPERATION

CROSS-REFERENCE TO RELATED APPLICATIONS

This application is a continuation of U.S. patent application Ser. No. 12/254,748 entitled "Patient Monitor Having Context-Based Sensitivity Adjustments," filed Oct. 20, 2008, which is a continuation of U.S. patent application Ser. No. 11/071,875, entitled "Application Identification Sensor," filed Mar. 3, 2005, now U.S. Pat. No. 7,438,683, which claims a priority benefit under 35 U.S.C. §119(e) from U.S. Provisional Patent Application No. 60/549,996, entitled "Application Identification Sensor," filed Mar. 4, 2004. The present application incorporates the entirety of the aforementioned priority documents herein by reference.

BACKGROUND OF THE INVENTION

Pulse oximetry is a widely accepted noninvasive procedure for measuring the oxygen saturation level of arterial blood, an indicator of a person's oxygen supply. A typical pulse oximetry system has a sensor, a monitor and a patient cable providing a communication path between the sensor and monitor. The sensor is adapted to attach to a tissue site, such as a patient's finger, and respond to hemaglobin constituents of pulsatile blood. The monitor is adapted to receive a physiological signal from the sensor and provide a numeric readout of the patient's oxygen saturation and pulse rate.

SUMMARY OF THE INVENTION

A conventional pulse oximetry monitor processes the physiological signal from the sensor based upon sensor calibration data, internal algorithm parameters and user-selectable operational parameters. The sensor may have an information element that is readable by the monitor and that identifies one or more characteristics of the sensor. These characteristics may relate to sensor components, such as emitter wavelength, or the sensor type, such as adult, pediatric or neo-natal. The monitor may select calibration data and internal parameters accordingly. An information element may be a passive device, such as a resistor, or an active device, such as a transistor network, a logic device or a memory chip. An information element is described in U.S. Pat. No. 5,758,644 entitled Manual and Automatic Probe Calibration, which is assigned to Masimo Corporation, Irvine, Calif. and incorporated by reference herein.

One aspect of an application identification sensor comprises a plurality of emitters configured to transmit light into a tissue site and a detector configured to receive the light after tissue absorption. The detector generates a signal responsive to the intensity of the light and communicates the signal to a monitor. An information element is readable by the monitor so as to identify a sensor application. The monitor presets at least one user-selectable operational parameter in response to the information element. In one embodiment, the application relates to emergency care and the user-selectable operational parameter is selected from the set of sensitivity and averaging time.

Another aspect of an application identification sensor is a method where a sensor is attached to a monitor and an information element is read. Data from the information element is associated with an application, and user-selectable parameters corresponding to the application are preset. In one embodiment, the application is identified as emergency related. In a particular embodiment, maximum sensitivity and minimum averaging time are selected for processing a signal from the sensor.

An aspect of an application identification apparatus comprises a sensor configured to generate a physiological signal and a monitor capable of processing the physiological signal so as to measure a physiological parameter responsive to a constituent of pulsatile blood. The monitor has an application identification input. User-selectable operational parameters for said monitor have values responsive to the application identification input. In one embodiment, the application identification input is provided by an information element associated with the sensor and readable by the monitor. In another embodiment, the application identification input is provided by a user-actuated button associated with the monitor.

DETAILED DESCRIPTION OF THE PREFERRED EMBODIMENTS

Figure 1:
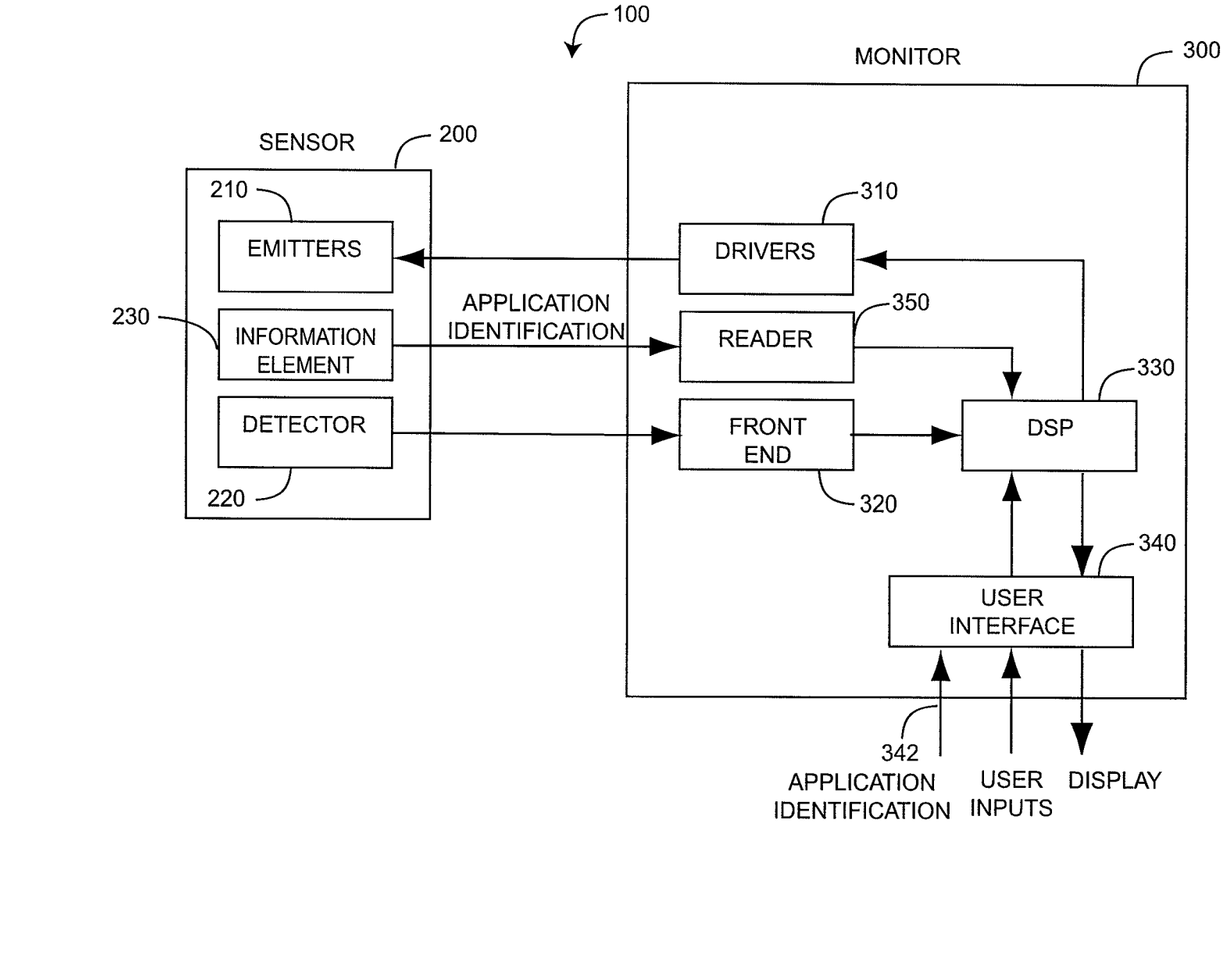
FIG. 1 is a block diagram a pulse oximetry system utilizing an application identification sensor or an application identification user input or both.

FIG. 1 illustrates a pulse oximetry system 100 incorporating an application identification sensor 200 and a monitor 300 adapted to recognize the sensor 200 accordingly. The sensor 200 has emitters 210 adapted to transmit light into a tissue site and a detector 220 adapted to receive light after absorption by the tissue site and to generate a detector signal in response, as is well known in the art. The monitor 300 has drivers 310 that activate the emitters 210 and a front-end 320 that conditions and digitizes the detector signal for input into a digital signal processor (DSP) 330, as is also well known in the art. The DSP 330 computes oxygen saturation and pulse rate and provides the results on a display. A user interface 340 allows a user to input selected operational parameters for the DSP 330. A pulse oximeter monitor is described in U.S. Pat. No. 6,699,194 entitled Signal Processing Apparatus and Method and U.S. Pat. No. 6,650,917 entitled Signal Processing Apparatus, which are assigned to Masimo Corporation, Irvine, CA and incorporated by reference herein. A user interface is described in U.S. Pat. No. 6,658,276 entitled Pulse Oximeter User Interface, which is assigned to Masimo Corporation, Irvine, Calif. and incorporated by reference herein.

Also shown in FIG. 1, the application identification sensor 200 also has an information element 230, and the monitor has a corresponding information element reader 350. Advantageously, the sensor 200 is manufactured with an information element 230 that identifies a particular application to the monitor 300. The monitor 300 presets one or more user-selectable operational parameters accordingly. This reduces or eliminates the need for user input of operational parameters specific to a particular application. In an alternative embodiment, the monitor 300 has an application identification button, switch or other user-actuated device 342 that causes the monitor 300 to preset one or more user-selectable operational parameters.

In one particularly advantageous embodiment, the application identification sensor 200 is manufactured, packaged and/or labeled for use in a trauma or emergency care situation, and the information element 230 is configured to identify that application or use to the monitor 300 accordingly. For example, when such a sensor 200 is connected to the monitor 300, the monitor 300 may select maximum sensitivity and minimum averaging time, providing hands-off optimum settings for these user-selectable operational parameters for a trauma care application. In an alternative embodiment, the monitor 300 has an application identification button 342 that is labeled for use in trauma or emergency care situations and that, when actuated, causes the monitor 300 to set user-selectable operational parameters accordingly.

For various applications, an application identification sensor 200 may indicate other user-selectable operational parameters relating to monitor alarms, displays, outputs and general characteristics to name a few. Alarm parameters may include alarm limits, delay and volume, for example. Display parameters may regard numeric, plethysmograph and trend formats to name a few. Output parameters may include, for instance, the analog output and alarm output types and digital output data formats. General characteristics may include operational modes such as maximum sensitivity and minimum averaging time cited above. General characteristics may also include averaging mode, such as described in U.S. Pat. No. 6,430,525 entitled Variable Mode Averager, which is assigned to Masimo Corporation, Irvine, Calif. and incorporated by reference herein. General characteristics may further include, for example, user key lock-out and password entry to enable user keys and other monitor functions.

An application identification sensor has been disclosed in detail in connection with various embodiments. These embodiments are disclosed by way of examples only and are not to limit the scope of the claims that follow. For example, although an application identification sensor has been described with respect to a pulse oximetry system, a sensor having an information element that identifies an application to a monitor can be utilized in systems capable of measuring physiological parameters other than or in addition to oxygen saturation and pulse rate. One of ordinary skill in art will appreciate many other variations and modifications.

What is claimed is:

1. A patient monitoring system, comprising:
   a noninvasive optical sensor configured to detect light attenuated by body tissue of a monitored patient and provide a detector signal indicative of one or more physiological parameters of the monitored patient based at least in part on the detected light;
   a monitor configured to receive the detector signal and configured to operate in a plurality of applications, each of the applications including two or more user-selectable operation parameters separately configurable through a user interface, wherein the monitor is further configured to calculate a measurement output responsive to said detector signal; and
   a single dedicated mechanical actuator configured to select one of the plurality of applications, wherein upon actuation of the single dedicated mechanical actuator, the monitor is automatically configured according to the two or more user-selectable operation parameters associated with the selected one of the plurality of applications, and wherein said automatic configuration of the monitor is not dependent upon the user interface.

2. The patient monitoring system of claim 1, wherein one of the plurality of applications is an emergency mode application.

3. The patient monitoring system of claim 1, wherein the two or more user-selectable operation parameters include a sensitivity.

4. The patient monitoring system of claim 3, wherein the sensitivity comprises a maximum sensitivity setting.

5. The patient monitoring system of claim 3, wherein the sensitivity determines how closely the measurement output from the monitor follows a most recent measurement output calculated by the monitor.

6. The patient monitoring system of claim 1, wherein the two or more user-selectable operation parameters include averaging time.

7. The patient monitoring system of claim 6, wherein the averaging time comprises a minimum averaging time setting.

8. The patient monitoring system of claim 1, further comprising a sensor, wherein the sensor comprises an information element configured to identify a particular application to the monitor.

9. The patient monitoring system of claim 8, wherein the sensor is packaged for use in an emergency care application.

10. The patient monitoring system of claim 1, wherein the single dedicated mechanical actuator comprises a user-actuated input device.

11. The patient monitoring system of claim 10, wherein the user-actuated input device comprises a button.

12. The patient monitoring system of claim 10, wherein the user-actuated input device comprises an input switch.

13. A method of configuring a patient monitor based at least in part on an environment of use of said patient monitor, the method comprising:
   receiving from a noninvasive optical sensor electronic signals indicative of one or more physiological parameters of a monitored patient, said electronic signals indicative of light attenuated by body tissue of the monitored patient;
   receiving from an actuation of a single dedicated mechanical actuator of a patent monitor a monitor configuration input indicative of an application in said patient monitor, said patient monitor configured to operate in a plurality of applications, wherein upon said actuation of the single dedicated mechanical actuator, the patient monitor is automatically configured according to two or more user-selectable operation parameters based at least in part on the monitor configuration input, the two or more user-selectable operation parameters separately configurable through a user interface, wherein said automatic configuration of the patient monitor is not dependent upon the user interface; and
   processing with a signal processor said electronic signals according to the automatic configuration of the two or more user-selectable operation parameters to determine output measurements for the one or more physiological parameters of said monitored patient.

14. The method of claim 13, wherein one of the plurality of applications is an emergency care application.

15. The method of claim 13, wherein the two or more user-selectable operation parameters include a sensitivity.

16. The method of claim 13, wherein the two or more user-selectable operation parameters include averaging time.

* * * * *

UNITED STATES PATENT AND TRADEMARK OFFICE
CERTIFICATE OF CORRECTION

PATENT NO. : 9,161,713 B2
APPLICATION NO. : 13/721497
DATED : October 20, 2015
INVENTOR(S) : Al-Ali et al.

It is certified that error appears in the above-identified patent and that said Letters Patent is hereby corrected as shown below:

On the title page

Page 1 item 72, line 4, change "Laguna Hils," for Walter M. Weber to --Laguna Hills,--.

Column 2 page 1, item 56 line 11, change "Sensitifity" to --Sensitivity--.

Column 1 page 7, item 56 line 37, change "Nonnigringement" to --Noninfringement--.

Column 2 page 7, item 56 line 47, change "cv00080" to --cv-00080--.

Column 2 page 7, item 56 line 71, after "Doc." delete "Doc".

Column 2 page 8, item 56 line 26, change "Phillips" to --Philips--.

In the specification

Column 1 line 29, change "hemaglobin" to --hemoglobin--.

In the claims

Column 4 line 38, Claim 13, change "patent" to --patient--.

Signed and Sealed this
Second Day of August, 2016

Michelle K. Lee
*Director of the United States Patent and Trademark Office*